US00PP35397P2

(12) United States Plant Patent
Valin

(10) Patent No.: US PP35,397 P2
(45) Date of Patent: Sep. 26, 2023

(54) ***WEIGELA* PLANT NAMED 'TMWG17-18'**

(50) Latin Name: *Weigela florida*
Varietal Denomination: TMWG17-18

(71) Applicant: Charles Valin, Ipswich (GB)

(72) Inventor: Charles Valin, Ipswich (GB)

( * ) Notice: Subject to any disclaimer, the term of this patent is extended or adjusted under 35 U.S.C. 154(b) by 0 days.

(21) Appl. No.: 17/992,001

(22) Filed: Nov. 22, 2022

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new cultivar of *Weigela* plant named 'TMWG17-18' that is characterized by its compact mounding growth habit, dark olive-green emerging spring foliage, very dark purple summer foliage which is almost black when exposed to direct sun, red-purple flower buds, and dark pink tubular flowers borne in cymes ranging from eight to fourteen flowers per cyme.

2 Drawing Sheets

Genus and species: *Weigela florida.*
Variety denomination: 'TMWG17-18'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'TMWG17-18'.

The new cultivar 'TMWG17-18' originated from a *Weigela* breeding program which the inventor carried out at the inventor's nursery in Ipswich, United Kingdom. The inventor raised 'TMWG17-18' from seed collected from the open-pollination of proprietary seedling code 'WG14006' as the female parent (unpatented). The male parent is an unidentified proprietary unpatented seedling raised by the inventor and retained in the inventor's collection of breeding material. 'TMWG17-18' was developed and selected by the inventor for its compact mounded plant habit, very dark foliage which is almost black in direct sun, and dark pink flowers.

The inventor selected 'TMWG17-18' in 2018. 'TMWG17-18' was raised by the inventor at a greenhouse and field nursery in Ipswich, Suffolk, United Kingdom.

The inventor first asexually reproduced 'TMWG17-18' in 2018 by the method of softwood cuttings. Asexual reproduction took place in Ipswich, Suffolk, United Kingdom. Since that time, the unique characteristics of the new *Weigela* plant have been confirmed as uniform and stable and to reproduce true to type in successive generations of asexual reproduction.

SUMMARY

The following traits have been repeatedly observed and represent the characteristics of the new *Weigela* cultivar 'TMWG17-18'. 'TMWG17-18' has not been tested under all possible conditions and phenotypic differences may be observed with variations in environmental, climatic and cultural conditions.

1. 'TMWG17-18' exhibits a compact mounding growth habit.
2. After two years of growth in a 3-gallon container, plants of 'TMWG17-18' achieve a height of 70 cm to 75 cm and a width of 75 cm to 80 cm.
3. The emerging spring foliage color 'TMWG17-18' is dark olive-green in color.
4. In the summer months, when exposed to direct sun, the foliage of 'TMWG17-18' becomes very dark purple, almost black, in color.
5. The buds of 'TMWG17-18' are dark red-purple in color.
6. The flowers of 'TMWG17-18' consist of five petals with flared petal lobes which are dark pink in color.
7. The inflorescences of 'TMWG-17-18 consist of flowers borne in cymes ranging from eight to fourteen flowers per cyme.
8. 'TMWG17-18' flowers profusely in mid-spring and then sporadically during summer.
9. 'TMWG17-18' grows well in moist well-drained soils in full sun to partial shade.
10. 'TMWG17-18' is hardy at least to USDA Zone 5.

BRIEF DESCRIPTION OF THE PHOTOGRAPHS

The accompanying color photographs illustrate the overall appearance of the new *Weigela* variety 'TMWG17-18' showing colors as true as it is reasonably possible to obtain in colored reproductions of this type. Colors in the photographs may differ from the color values cited in the detailed botanical description, which accurately describe the observed colors of the new variety 'TMWG17-18'.

Figure 1:
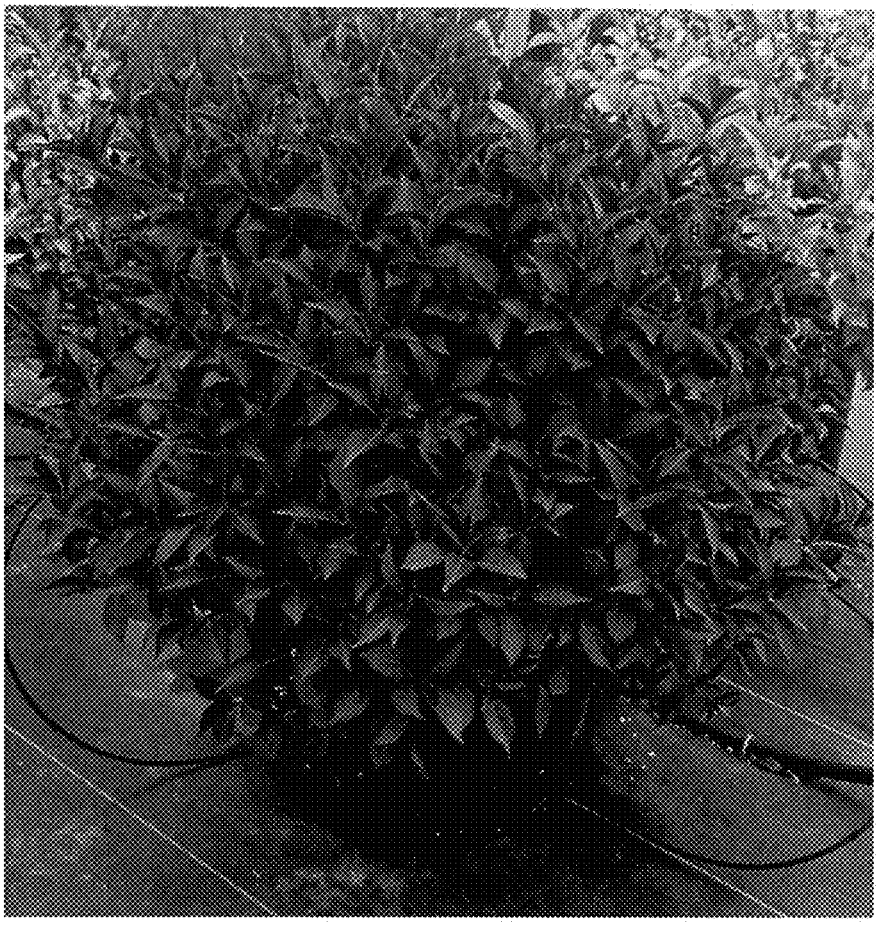
FIG. 1 depicts a two years old plant of 'TMWG17-18' in early spring before flowering.
Figure 2:
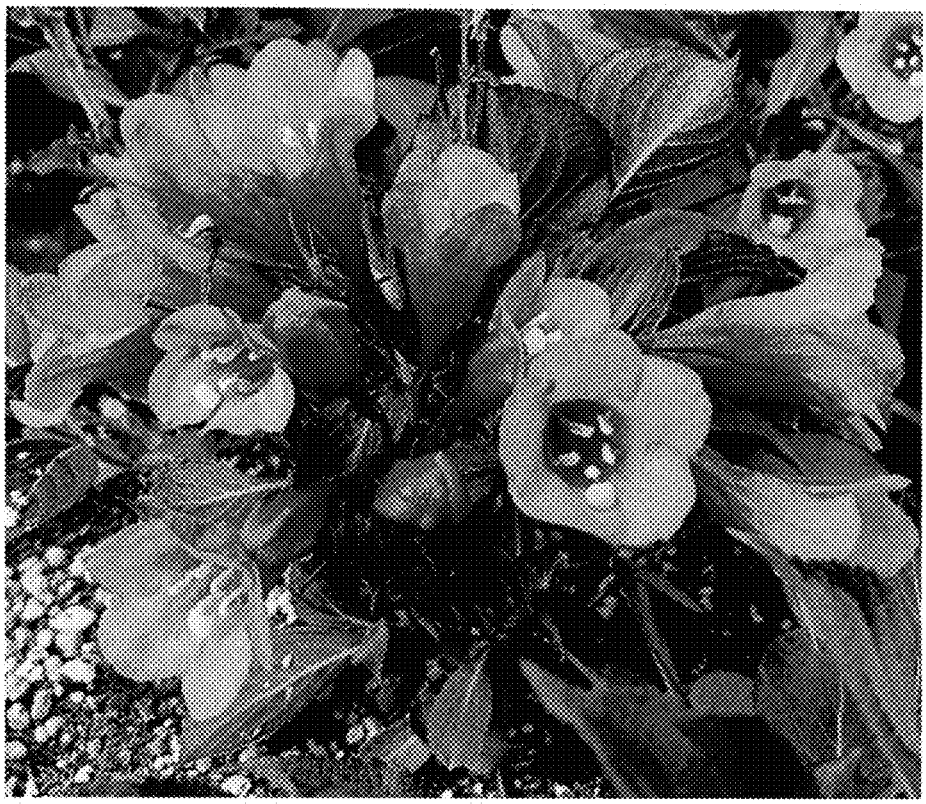
FIG. 2 depicts a one year old plant of 'TMWG17-18' in early summer when the plant is in bud and flower.

Both photographs were taken in Santa Barbara, Calif. where the plants were growing entirely outdoors under light shade cloth. No chemicals were used to treat the plants.

BOTANICAL DESCRIPTION OF THE PLANT

The following is a detailed description of the new cultivar 'TMWG17-18'. Data was collected from a two-year old plant grown in a 3-gallon container in mid-summer under light shade in Santa Barbara, Calif. The color determinations are in accordance with the 2007 edition of The Colour Chart of The Royal Horticultural Society, London, England, except where general color terms of ordinary dictionary significance are used. No chemicals were used to treat the plant.

Botanical classification: *Weigela.*

*Variety.*—'TMWG17-18'.

*Species.*—florida.

Plant description:

*Growth habit.*—Compact, mounding.

*Use.*—In containers and in the landscape.

*Suitable container sizes.*—1 to 3 gallon containers.

*Dimensions in second year in a 3-gallon container.*—70 cm to 75 cm in height, and 75 cm to 80 cm. in width.

*Hardiness.*—At least hardy to USDA Zone 5.

*Propagation.*—Semi-ripe stem cuttings.

*Time to initiate roots.*—4 to 5 weeks are required to produce roots on an initial cutting.

*Crop time.*—9-10 months to produce a first year flowering plant in a one gallon container, and two years to produce a fully filled out flowering plant in a 3 gallon container.

*Root system.*—Fibrous.

*Light.*—Plant in full sun or light shade.

*Soil.*—Plant in moist but well drained soil.

*Type.*—Deciduous shrub.

*Seasonal interest.*—Very dark foliage in full sun or light shade.

Stem:

*Shape.*—Terete.

*Dimensions.*—5 cm in length, 1.5 cm in diameter at soil level.

*Color.*—197C.

*Surface.*—Lignified in second year, rough, glabrous, lenticels present.

*Lenticels.*—Spaced approximately 5 mm apart, raised 0.5 mm above stem surface, narrowly elliptic, 2 mm in length, 1.5 mm in width, color as stem, 197C.

Branches:

*Description.*—All branches arise from the base of the plant, at or below the initial pinch or stopping of the first growth.

*Quantity.*—Approximately 30 basal branches.

*Branch stem length.*—55 cm to 65 cm in length. First leaves borne at 20 cm-25 cm.

*Branch stem diameter.*—8 mm below first leaves.

*Shape.*—Terete.

*Internode length.*—Variable, between 1.5 cm and 4 cm.

*Color (current year's growth).*—173A (older, lower stem section), 187B (new upper stem growth).

*Color (previous year's growth).*—197C.

*Surface.*—Smooth, pubescent, hairs fine and short, less than 0.5 mm in length, hair color 156B.

*Lenticels.*—Present on previous year's stems only, spaced approximately 5 mm apart, raised 0.5 mm above stem surface, narrowly elliptic, 2 mm in length, 1.5 mm in width, color 197C.

Foliage:

*Leaf arrangement.*—Opposite.

*Leaf division.*—Simple.

*Leaf shape.*—Ovate, longitudinally inwardly curved.

*Leaf attachment.*—Sessile or short petiolate.

*Petioles (where present).*—Shape: Sulcate, adaxial surface concave. Dimensions: Up to 4 mm in length and 1.5 mm in width. Color: 144C. Margins: Puberulent, hairs very short and fine, color NN155D.

*Leaf dimensions.*—60 mm in length, 25 mm in width.

*Leaf surface (both).*—Glabrous.

*Leaf color (spring growth, both surfaces).*—147A-147B.

*Leaf color (summer foliage, full sun or light shade, adaxial surface).*—Ranges between N187A or darker and 187A.

*Leaf color (summer foliage, abaxial surface).*—Mottled, leaf surface divided into small inter-veinal irregular sections, light green 192A in color, bounded by contrasting dark purple veins, color 187A.

*Leaf apex.*—Acute.

*Leaf base.*—Cuneate.

*Leaf margin.*—Finely serrate, teeth 1 mm-1.5 mm apart, depth 0.5 mm, glabrous.

*Leaf venation pattern.*—Pinnate.

*Veins (adaxial surface).*—Slightly depressed, color 144C.

*Veins (abaxial surface).*—Midrib prominently raised, lateral veins less so. Midrib color 184B, vein color 187A.

Inflorescence:

*Inflorescence form.*—Cymose.

*Quantity of inflorescences per plant (peak flowering, late spring).*—Approximately 30.

*Quantity of flowers per inflorescence.*—8-14.

Flowers:

*Flower shape.*—Salverform.

*Flower aspect.*—Outward and upward facing.

*Length of flower.*—30 mm.

*Diameter of flower (at flower tube apex).*—15 mm.

*Bud.*—Shape: Club-shaped. Color: 59B. Dimensions (including corolla tube): 25 mm-30 mm in length (including corolla tube), 9 mm in diameter (at bud apex immediately prior to opening). Surface: Glabrous, matte.

*Bracteoles.*—Arrangement: Borne in pairs the base of peduncle. Shape: Narrowly lanceolate. Dimensions: 8mm-10 mm in length, 1 mm in width. Color (adaxial surface): 147B. Color (abaxial surface); 192A. Surface: Glabrous.

*Peduncle.*—Dimensions: 14 mm in length and 1 mm in diameter. Shape: Terete. Color: 197C. Surface: Glabrous with faint longitudinal ridges.

*Calyx, sepals.*—Shape: Funnel-shaped. Calyx diameter: 5 mm-6 mm measured across sepal apices. Sepals: 5 in number, fused towards and at base. Sepal dimensions: 6 mm in length, 1.5 mm in width. Sepal color (both surfaces): 147B. Sepal surface (both surfaces): Matte, faintly puberulent.

*Corolla.*—Shape: Tubulate. Dimensions: 30 mm in length, 2 mm in diameter at base, 15 mm in diameter at base of petal lobes. Surface: Glabrous. Tube color (both surfaces): 59A.

*Petals.*—Description: 5 petals, longitudinally fused then lobed and free, rotate. Lobe shape: Orbicular. Lobe color (both surfaces): 59C at base, otherwise 70C with splashes 59C. Surface texture: Glabrous.

Reproductive organs:

*Stamens.*—Quantity: 5, fused at base. Filaments: 11 mm in length, 0.5 mm-0.75 mm in diameter. Filament color: 59C towards base, becoming 70C towards anthers. Anther: Shape narrowly elliptical, 4 mm in length, 0.75 mm in width, centrally dorsifixed. Anther color: 163D. Pollen: None observed.

*Pistils.*—Quantity: 1. Style: Terete, 23 mm in length and 0.5 mm in diameter. Style color: 70C towards base, N155D centrally, 59D below stigma. Style surface: Glabrous. Stigma shape: Capitate, three-lobed. Stigma dimensions: 2.5 mm in width and 2 mm in height. Stigma color: 162D.

*Ovary.*—Minute, appears undeveloped.

Seed: None observed.

Susceptibility or resistance to pests and diseases: None.

COMPARISON WITH PARENTAL LINES AND CLOSEST KNOWN VARIETY

Whereas both the female parent variety 'WG14006' and 'TMWG17-18' exhibit similar habits with dark foliage and pink flowers, the foliage of 'TMWG17-18' becomes darker than 'WG14006', almost black in mid-summer and 'TMWG17-18' blooms more profusely than 'WG14006' in spring. Since the identity of the male parent is unknown, no comparison is available.

The variety of dark-leafed *Weigela* which the inventor considers to be closest in appearance to 'TMWG17-18 is *Weigela* 'Elvera' (U.S. Plant Pat. No. 12,217). Both 'Elvera' and 'TMWG17-18' exhibit very dark purple foliage in their mature stage. The inventor has observed that the plant habit of 'Elvera' is low and spreading whereas plants of 'TMWG18-18' are rounded with similar height and spread. In addition, under the same growing conditions, the inventor has observed that the foliage of 'TMWG17-18' is darker, almost black, in full sun whereas the foliage of 'Elvera' remains dark red-purple.

I claim:

1. A new and distinct cultivar of *Weigela* plant named 'TMWG17-18' as described and illustrated herein.

* * * * *